(12) United States Patent
White et al.

(10) Patent No.: US 8,353,841 B2
(45) Date of Patent: *Jan. 15, 2013

(54) APPARATUS AND METHOD FOR SENSOR DEPLOYMENT AND FIXATION

(75) Inventors: Jason White, Decatur, GA (US); Kelly Tumlin, Conyers, GA (US)

(73) Assignee: CardioMEMS, Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/286,641

(22) Filed: Nov. 1, 2011

(65) Prior Publication Data

US 2012/0046560 A1 Feb. 23, 2012

Related U.S. Application Data

(63) Continuation of application No. 11/232,668, filed on Sep. 22, 2005, now Pat. No. 8,118,749.

(60) Provisional application No. 60/658,358, filed on Mar. 3, 2005, provisional application No. 60/662,210, filed on Mar. 14, 2005.

(51) Int. Cl.
*A61B 5/02* (2006.01)

(52) U.S. Cl. ................. 600/486; 600/485; 600/481

(58) Field of Classification Search ............ 600/485–486
See application file for complete search history.

(56) References Cited

U.S. PATENT DOCUMENTS

| 7,572,228 B2 * | 8/2009 | Wolinsky et al. | 600/486 |
| 2003/0216622 A1 * | 11/2003 | Meron et al. | 600/300 |

* cited by examiner

*Primary Examiner* — Patricia Mallari
*Assistant Examiner* — Michael D'Angelo
(74) *Attorney, Agent, or Firm* — Ballard Spahr LLP

(57) ABSTRACT

An implant assembly is implanted in vivo within a vascular system in the implant assembly has a diameter greater than a vessel and compliance characteristics such that, upon release, the implant assembly forms an interference fit is between the anchor structure and the vessel wall, thereby preventing further distal movement.

27 Claims, 10 Drawing Sheets

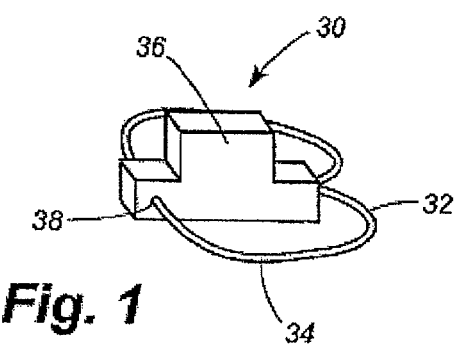
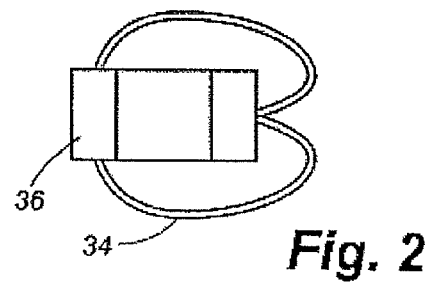
Fig. 1
Fig. 2
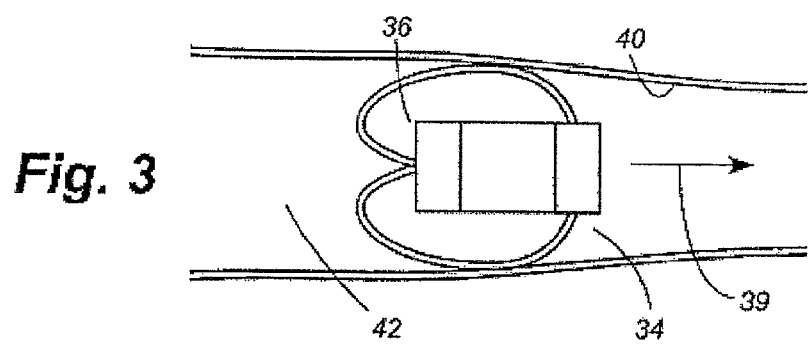
Fig. 3
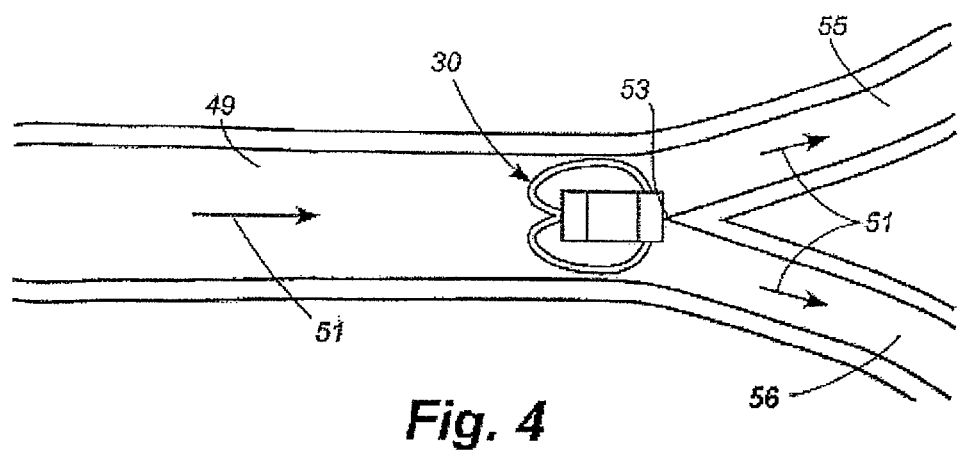
Fig. 4

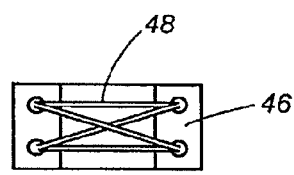
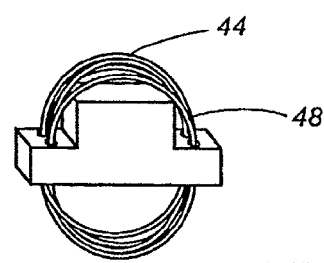
Fig. 12         Fig. 13
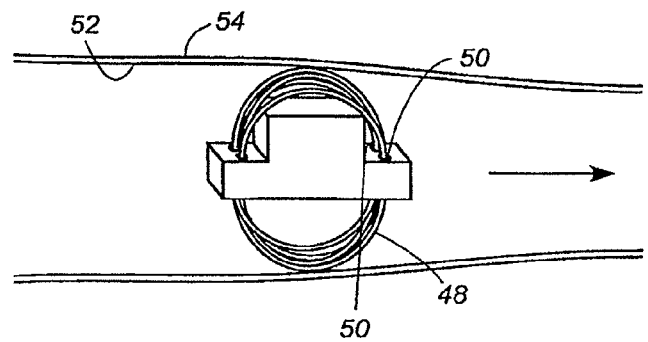
Fig. 14
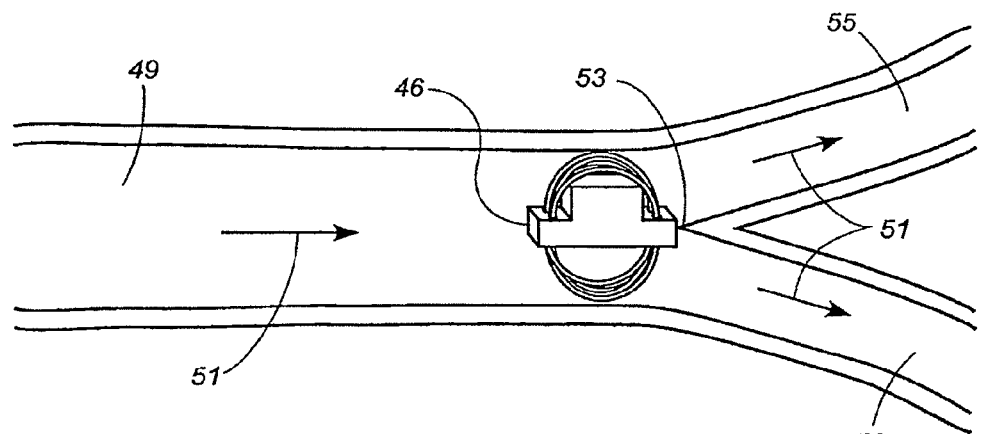
Fig. 15

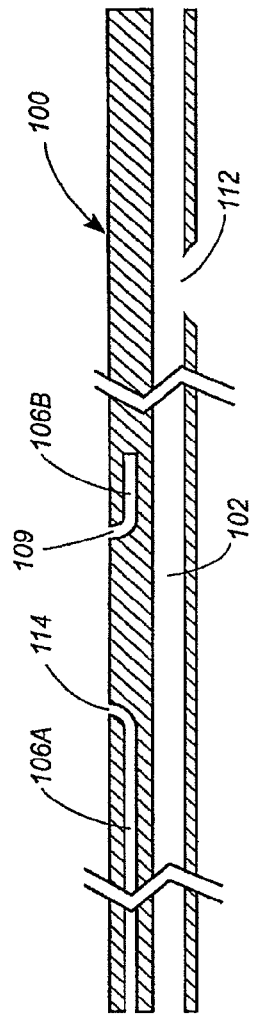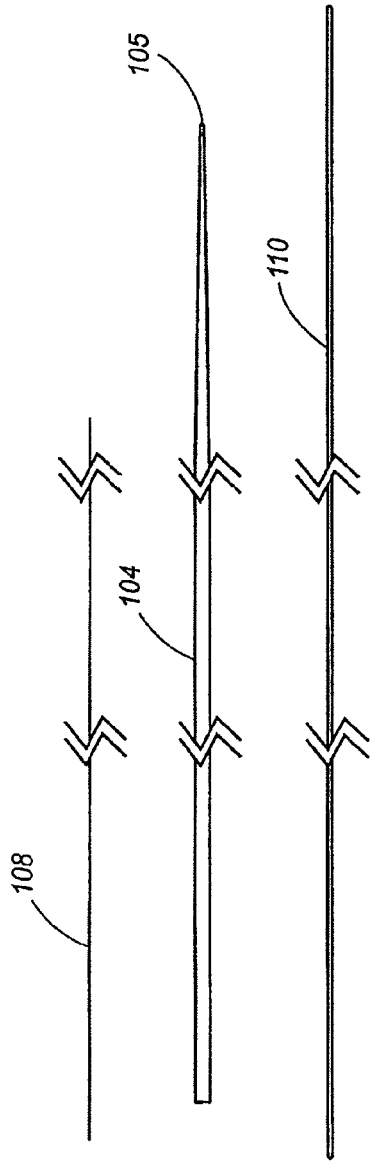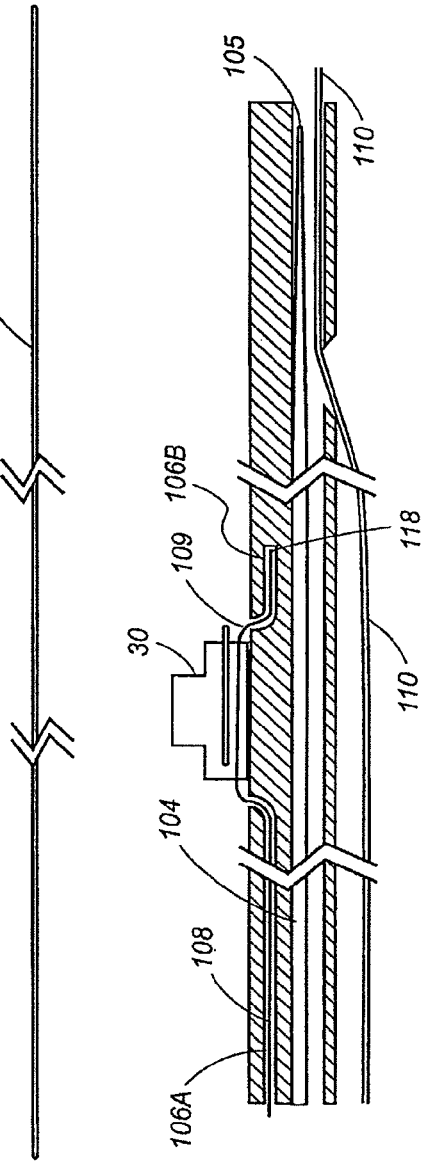
Fig. 25
Fig. 26
Fig. 27
Fig. 28
Fig. 29

APPARATUS AND METHOD FOR SENSOR DEPLOYMENT AND FIXATION

CROSS-REFERENCE TO RELATED APPLICATIONS

This application is a continuation application of U.S. Utility application Ser. No. 11/232,668, filed Sep. 22, 2005, which claims the benefit of U.S. Provisional Application No. 60/658,358, filed Mar. 3, 2005 and to U.S. Provisional Application No. 60/662,210, filed Mar. 14, 2005, which applications are herein incorporated by reference in their entirety.

FIELD OF INVENTION

This invention relates generally to implantation of intracorporal devices into vessels, and to fixing the devices, either permanently or temporarily, within the vessel.

BACKGROUND OF THE INVENTION

In recent years, the long-sought goal of implantable biosensors has begun to see realization and, in some cases, clinical use. As this concept has seen continued research and development, issues regarding intracorporal fixation of the sensor have come to light. Particularly within blood vessels, the sensor is subjected to a continuous, pulsatile flow. This is a difficult environment in which to secure a sensor or other apparatus reliably without unduly restricting blood flow or impairing the vessel wall. One major vessel of interest in the realm of cardiology is the pulmonary artery. The pulmonary artery is a particularly challenging location in which to secure an intracorporal device because, in addition to the above considerations, the vessel is especially thin, compliant and prone to perforation.

Design considerations for an ideal fixation device intended for intravascular fixation are outlined as follows. The fixation device should be passive and maintain a separation distance between the sensor and the vessel wall to maintain blood flow past the sensor. The deployed size and radial strength of the device should be sufficient to prevent its migration into vessels that would be occluded by the dimensions of the sensor while creating minimal stress concentrations where the fixation device contacts the vessel wall. Alternatively, intracorporal devices can be designed sufficiently small in size so that when deployed in organs or regions with sufficiently redundant blood flow, the device can embolize on its own without harming the organ or the host. Finally, the fixation device should be sufficiently versatile as not to depend, within physiologically relevant ranges, on the size of the vessel in order to maintain its position.

There have been attempts to create devices intended to hold intracorporal devices fixedly within vessels. Several such attempts are described in patent publication number US 2004/0044393 and in European patent application number EP0928598. These attempts fall short of meeting all of the necessary requirements outlined above.

Prior art devices include a self-expansible stent on which an intracorporal device is mounted. This stent maintains a known length when implanted in a vessel where only the approximate diameter can be determined. Other devices and methods include fixation of a sensor in a bodily lumen, in which the sensor support is coupled to a fixation device. The fixation device is a stent or ring, has a sensor support coupled thereto and is intended to be sutured to the vessel wall or held in place by plastically deforming the structure using a balloon catheter. The ring is essentially a stent with an abbreviated length and suffers from the same shortcomings as traditional stent devices.

A stent is designed with mechanical characteristics that enable it to hold open diseased vessels post dilation. Therefore, the radial strength of the stent is greater than the inward radial forces exerted during vessel recoil. This primary requirement leads to a mismatch in compliance, with that of the stent dominating. Subsequently, stress concentrations are created at the interface of the stent and vessel. These stress concentrations are greatest at the terminal ends of the stent where there is an abrupt transition in stiffness between the stented and unstented segments of the vessel. Because undiseased vessels are usually more compliant compared to diseased ones, this compliance mismatch is amplified when placing a stent in healthy vasculature. Along similar lines, accurate stent sizing in the vessel is critical, especially in the case of the pulmonary artery. Accurate stent sizing to prevent migration and to avoid perforation of the vessel wall could be more difficult in healthy vasculature, especially the pulmonary artery, which has a smooth inner lining and greater compliance than most vessels. Thus, the physician must be conscious of the particulars of vessel compliance along with stent recoil and radial strength to choose the best stent expanded diameter for a given vessel. This determination presents its own set of challenges and requires an unnecessary increase in complexity, e.g., in deployment, and risk of complication. Therefore, the use of a stent to maintain an intracorporal device in a vessel is not optimal.

Thus, a need exists for devices and methods for fixing intracorporal devices which satisfy the design requirements described herein. Furthermore, a need exists to deliver and fix such devices in a safe, simple and predictable manner.

SUMMARY OF THE INVENTION

Stated generally, this invention comprises an apparatus and method of deployment and fixation of an implant assembly by using a delivery apparatus to deliver an intracorporal device to a deployment site and fixation of the device using an anchoring structure. The intracorporal device may be either a wired or a wireless device.

Thus it is an aspect of this invention to provide an implant assembly having an anchoring structure for fixation within a vessel.

A further aspect of this invention is to provide an implant assembly adapted to be delivered via a delivery apparatus, such as a catheter.

Other objects, features, and advantages of the present invention will become apparent upon reading the following specification, when taken in conjunction with the drawings and the appended claims.

BRIEF DESCRIPTION OF THE DRAWINGS

FIG. 1 is an isometric view of a first embodiment of an implant assembly of this invention having two opposed wire loops.

FIG. 2 is a top view of the implant assembly of FIG. 1.

FIG. 3 is a cutaway view of a vessel showing the implant assembly of FIG. 1 fixed therein according to a first embodiment of an implantation method.

FIG. 4 is a cutaway view of a pulmonary arterial vessel showing the implant assembly of FIG. 1 fixed therein according to an alternate embodiment of an implantation method.

FIG. 12 is a top view of a fourth embodiment of an implant assembly of this invention having opposed wire loops.

FIG. 13 is an isometric view of the implant assembly of FIG. 12.

FIG. 14 is a cutaway view of a vessel showing the implant assembly of FIG. 12 fixed therein according to a first embodiment of an implantation method.

FIG. 15 is a cutaway view of a pulmonary arterial vessel showing the implant assembly of FIG. 12 fixed therein according to an alternate embodiment of an implantation method.

FIG. 25 is a side cross-sectional view of a delivery apparatus of this invention.

FIG. 26 is a side view of a tether wire of the delivery apparatus of this invention.

FIG. 27 is a side view of a core wire of the delivery apparatus of this invention.

FIG. 28 is a side view of a guidewire of the delivery apparatus of this invention.

FIG. 29 is a side cross-sectional view of the delivery system of this invention comprising the components of FIGS. 25-28.

DETAILED DESCRIPTION OF THE DISCLOSED EMBODIMENTS

Figure 5:
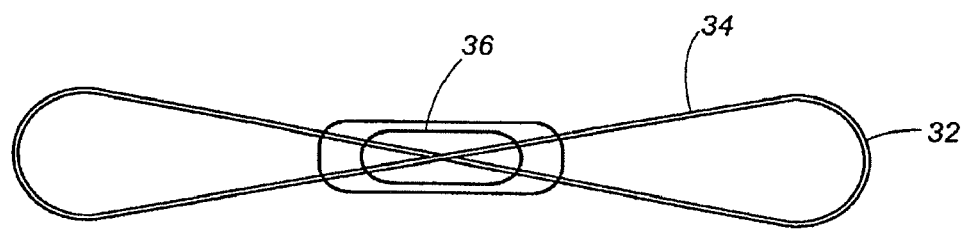
FIG. 5 is a top view of a second embodiment of an implant assembly of the invention having opposed wire loops.

An implant assembly of this invention includes an intracorporal device and an anchoring structure used to stabilize the intracorporal device in the body, such as in a vessel. Delivery systems of this invention are used to deploy and secure the implant assembly in a desired location in a vessel and include a delivery apparatus and an implant assembly. The intracorporal device may be a pressure sensor, further described below. The anchoring structure may be a structure capable of being introduced into the body via a delivery apparatus, such as a catheter, and then lodging within the vessel. Anchoring structures of this invention may include structure including opposed wire loops, radial wire array structures, and daisy petal structures, all further described below.

All of the implant assemblies of this invention obstruct approximately 50% or less of the cross-sectional area of the vessel in which it resides. Preferably, the implant assemblies obstruct 20% or less of the cross-sectional area of the vessel. Minimizing the obstruction of flow within the vessel allows the intracorporal device to remain secured in position in a vessel without creating significant impact to the flow within the vessel. Furthermore, all of the implant assemblies disclosed herein rely on the physical size of the expanded anchoring structure coupled with the stiffness of the wire used to construct the anchoring structure to prevent further distal movement. This is contrary to stent or vena cava filter type mechanisms wherein fixation is achieved by radially exerted force and/or hook or barb attachment features.

Anchoring structures of this invention may be formed from metal or polymer and may be in the form of a wire structure. The wire diameter of the anchoring structures of the current invention lies in the range of about 0.001 to about 0.015 inches. The material comprising the wire can be any biocompatible material known in the art that possess sufficient elastic properties to be useful for the purpose at hand. In one embodiment the material comprising the wire is a polymer. In an alternative embodiment the material comprising the wire may be a metal, such as nitinol, stainless steel, eligiloy, cobalt chrome alloys, or any other suitable metal. In a further embodiment, if the wire is comprised of a metal material, the biocompatible wire is coated with a dielectric material, such as, but not limited to, PTFE, polyurethane, parylene and diamond-like carbon (DLC) so as not to pose electromagnetic interference with the function of the intracorporal device when the device comprises an RF sensor. The term "wire" used throughout this document should be construed, without limitation, to embody the entire contents of this paragraph.

The phrase "intracorporal device" as used in this document includes any and all implantable devices. Such devices can include, e.g., sensors that measure chemical and/or physical parameters, devices configured to perform a function, e.g. drug delivery devices, and combinations of the same. The intracorporal device may communicate with external electronics either wirelessly or by being placed in physical contact with said electronics, such as by a wire.

The exemplary device disclosed herein describes a coating as a feature. It should be understood that this invention encompasses an intracorporal device constructed of a polymeric material and that the same construction techniques used to create the anchoring structures could be employed by threading the wires directly through the polymeric material comprising the device. Additionally, materials used in the construction of such intracorporal devices, coatings or otherwise, could be any biocompatible polymer. Such materials include but are not limited to biocompatible silicone rubber, FEP, PTFE, urethane, PVC, nylon, and polyethylene.

The intracorporal device used to couple to the anchoring structures described below has a width of about 0.5 to about 4 mm, a height of about 0.5 to about 4 mm, and a length of about 0.5 to about 12 mm. In one embodiment, the intracorporal device has a width of 3.2 mm, a height of 2 mm, and a length of 10 mm. Examples of such devices are disclosed in commonly owned U.S. Pat. No. 6,855,115; and in co-pending, commonly owned application Ser. Nos. 10/054,671; 10/886,829; 10/215,377; 10/215,379; 10/943,772 incorporated herein by reference.

Wire Loop Structures

One implant assembly of this invention adapted for deployment and fixation within a vessel includes an intracorporal device and a wire structure having wire loops. The loops may traverse the length of the device or may be limited to one end of the device. As shown in FIGS. 1 and 2, one embodiment of an implant assembly 30 having a double loop structure 32 includes a wire 34 attached to an intracorporal device 36 at an attachment site (not shown). The wire 34 is threaded through an end of the intracorporal device 36 at a hole 38. The anchor point is formed by crimping a piece of metal to the wire and trimming off the excess wire, so that the crimped-on metal comprises the terminal end of the wire. This metal end also provides a radiopaque marker for fluoroscopic visualization of the device.

After the wire 34 is threaded through the hole 38 on one end of the device, the wire is pulled with sufficient force to bury the anchor fixedly into the coating of the intracorporal device. The wire 34 is then looped around to form the double loop configuration 32. The second free end is also inserted under the coating and the anchor is buried in the coating to fix the anchor. In this manner, the ends of the wire are inserted under the coating of the intracorporal device 36.

FIG. 3 illustrates the deployment of the implant assembly 30 within a narrowing vessel. The arrow 39 shown in FIG. 3 indicates the direction of blood flow. After being released into the vessel, the wire loop 34 will contact the inner surface 40 of the wall of the vessel 42. Depending upon the configuration of the implant assembly 30 and the inner diameter of the vessel 42, this contact may occur immediately upon deployment. Alternatively the implant assembly can be configured so that the wire 34 of the implant assembly 30 does not initially contact the inner surface 40 of the vessel 42 but instead travels down the narrowing vessel until, at some point, the vessel narrows to such an extent that the wire loop 34 makes contact with the inner surface 40 of the vessel 42. Depending upon the compliance of the vasculature and the wire loop 34 of the implant assembly 30, the wire structure may compress radially inward or bow backwards as an interference fit is created. Or, depending upon the compliance of the wire comprising the implant assembly, the anchor structure 42 may yield, permitting the implant assembly 30 to travel further downstream. The implant assembly 30 will ultimately reach a point in the narrowing vessel 42 at which an interference fit between the wire loop 34 and the vessel will cause the implant assembly to lodge and to be held in place against any further movement.

An alternate method of anchoring an implant assembly 30 is based upon the principle of causing the intracorporal device to lodge at a furcation in a vessel of a patient. As an example, the pulmonary artery, which originates in the right ventricle, divides into the right and left pulmonary artery branches, one directed to each lung. These arteries divide and then subdivide, eventually to send arteries to all of the bronchopulmonary segments that form the different lobes of each lung. The pulmonary arterial vessels decrease in diameter significantly each time they divide.

The theory underlying the alternate method of anchoring an implant assembly is that the implant assembly, including the wire loops, can travel down a first vessel with the flow of blood, but when the implant assembly reaches a furcation, the implant assembly is too large to fit through either of the smaller branch vessels. The implant assembly thus lodges at the furcation, prevented from moving downstream by being too large and not sufficiently compliant to fit into the branch vessels, and prevented from moving upstream by the flow of blood through the arteries. In one embodiment, the implant assembly diameter is equal to or greater than the inner diameter of the first vessel. In this case, the implant assembly is sufficiently compliant so it does not produce an interference fit as it travels down the vessel but does preserve the intended orientation of the implant assembly when it reaches the subsequent furcation. In an alternate embodiment, the implant assembly diameter is less than the inner diameter of the arterial vessel such that no particular orientation is actively preserved but the implant assembly is too large and stiff to fit through subsequent branch vessels.

In either case, the implant assembly is configured such that, after a short period of time, e.g. 30 days, the deployment position is further reinforced by tissue overgrowth of the wire loops where they contact the vessel wall. At this point, the dominant fixation mechanism is the tissue to wire connection and the implant assembly cannot be easily removed without risk of damaging the vessel.

Referring to FIG. 4, the implant assembly 30 has been released into a first vessel 49. The implant assembly is free to travel through the first vessel 49 with the flow of blood in the direction indicated by the arrows 51. At a furcation 53, the first vessel 49 divides into smaller vessels 55, 56. Because the implant assembly 30 is substantially larger than the cross-section of any of the smaller vessels 55, 56, the implant assembly cannot proceed any further and lodges at the furcation 53.

Referring now to FIG. 5, a loop structure has a "figure eight" shape. An implant assembly 31 having a double loop structure 33 includes a wire 35 attached to the intracorporal device body 37 at an attachment site (not shown). The ends of the wire 35 are inserted under the coating of the intracorporal device body 37 as described in the previous example.

The purpose of the "figure eight" or double loop structure 33 is to stabilize the intracorporal device body from rotating or tumbling end-over-end within the vessel, thereby assuring that, in the case of a wireless sensing element comprising the intracorporal device, a coupling element of the intracorporal device body remains properly oriented with respect to optimal angles of interrogation via extracorporeal communication and data acquisition devices. The "figure eight" or double loop structure 33 of the disclosed embodiment measures approximately five centimeters in length. However, it will be appreciated that the preferred dimensions depend upon the inner diameter of the vessel into which it is being placed within relatively wide tolerances, and that the dimensions of the "figure eight" or double-loop structure 33 can be modified to adapt the device to any particular vessel. According to one aspect of the invention, the overall length of the intracorporal device body plus double-loop structure 33 is at least two times, and preferably at least about five times, the diameter of the vessel.

Figure 6:
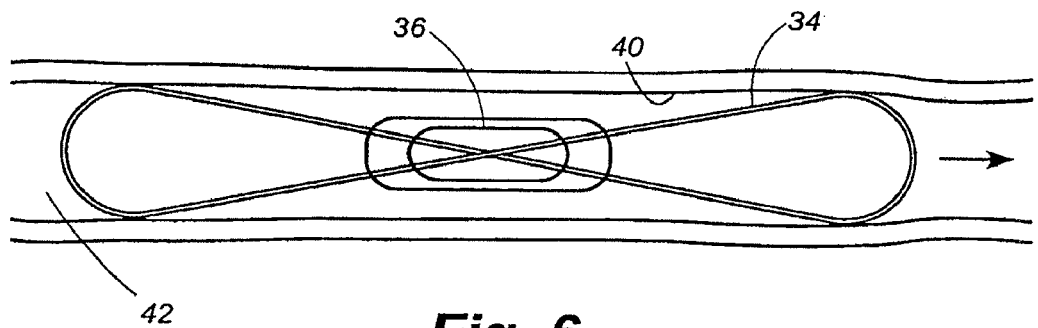
FIG. 6 is a cutaway view of a vessel showing the implant assembly of FIG. 5 fixed therein according to a first embodiment of an implantation method.

Referring to FIG. 6, upon deployment of the implant assembly 31 according to a first method, the implant assembly 31 is anchored by an interference fit between the wire 35 and the inner surface 41 of the wall of the vessel 43. The arrow 51 indicates the direction of blood flow.

Figure 7:
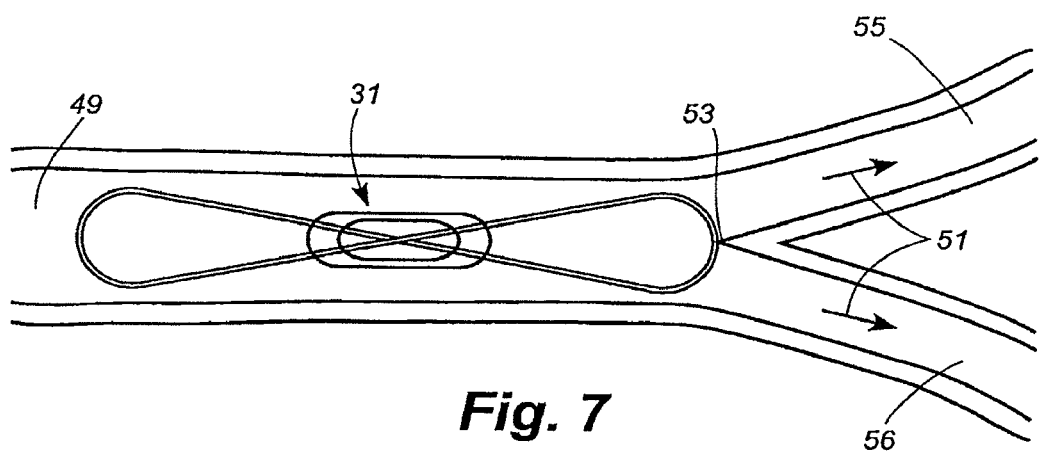
FIG. 7 is a cutaway view of a pulmonary arterial vessel showing the implant assembly of FIG. 5 fixed therein according to an alternate embodiment of an implantation method.

FIG. 7 illustrates an alternate method of anchoring the implant assembly 31, in which the implant assembly is deployed, e.g., into a first pulmonary arterial vessel 49 having a cross-section on the order of the cross-section of the implant 10 assembly. The implant assembly thus travels through the first vessel 49 in the direction of blood flow, indicated by the arrows 51. At a furcation 53, the first vessel 49 divides into smaller vessels 55, 56. Because the cross-section of the implant assembly 31 is substantially larger than the cross-section of either of the smaller vessels 55, 56, and not sufficiently compliant to deform further the implant assembly lodges at the furcation 53.

In the disclosed embodiment, the opposed loop structure 33 of the implant assembly 31 is constructed of a single wire. However, it will be understood that the opposed loop structure 33 can be constructed of more than one wire.

In alternative embodiments shown in FIGS. 8, 9, 12, and 13, the structure includes a plurality of wire loops 44 encircling an intracorporal device 46. The wire 48 is threaded from end to end in a circular fashion, through one or more holes 50 located on each end of the intracorporal device, to form the loops. Upon completion of the loop structure, the free end of the wire is used to create another anchor as described above. The second free end is then pulled back into the coating with sufficient force to bury the second anchor fixedly in the coating. In one embodiment, the location of the second anchor lies on the opposite side of the intracorporal device from the first anchor. This configuration is useful in order to position anchors away from a sensing or actuating element and/or to provide a means for determining the orientation of the device when viewed via fluoroscopic means. The wire loops are then arranged by mechanical means to create wire members that are substantially evenly distributed radially around the longitudinal axis of the intracorporal device.

Figure 8:
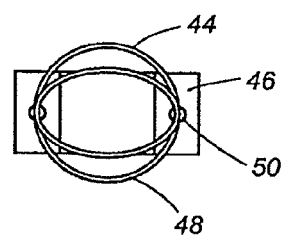
FIG. 8 is a top view of a third embodiment of an implant assembly of this invention having two opposed wire loops.
Figure 9:
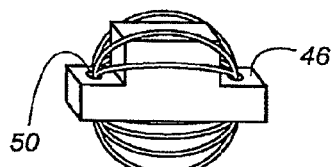
FIG. 9 is an isometric view of the implant assembly of FIG. 8.

The wire loops may be attached to the intracorporal device 40 by threading through one hole 50 located near the edge of the device 46 as referenced to the longitudinal axis of the device 46, as shown in FIG. 8. Alternatively, the wire loops may be attached to the intracorporal device 46 by threading through multiple holes 50 located near each edge of the device 46, as shown in FIG. 12.

Figure 10:
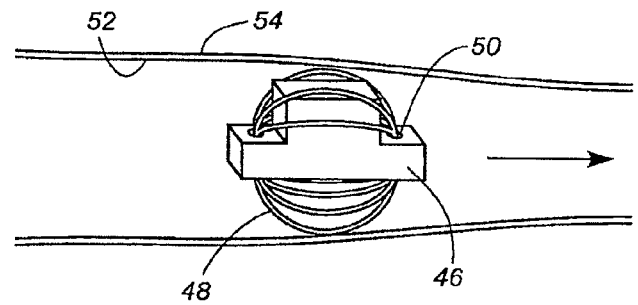
FIG. 10 is a cutaway view of a vessel showing the implant assembly of FIG. 8 fixed therein according to a first embodiment of an implantation method.
Figure 11:
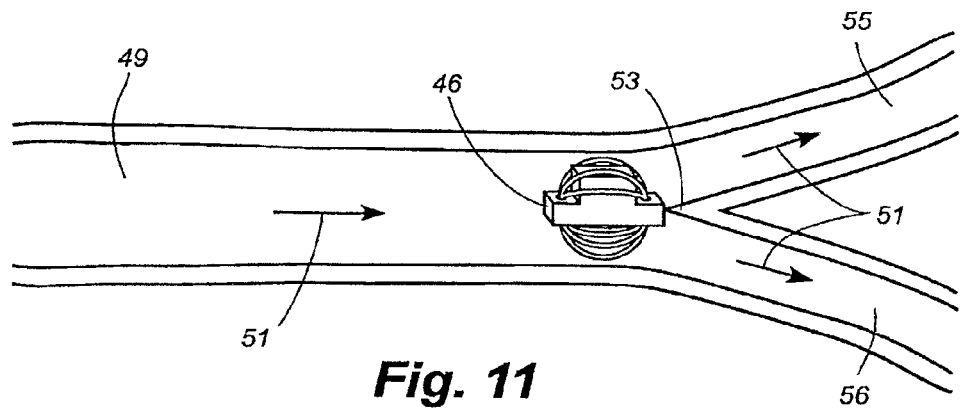
FIG. 11 is a cutaway view of a pulmonary arterial vessel showing the implant assembly of FIG. 8 fixed therein according to an alternate embodiment of an implantation method.

The implant assemblies of FIGS. 8, 9, 12, and 13 may be deployed according to either of the two methods described above. The implant assemblies can be configured so that they are anchored by an interference fit between the implant assemblies and the walls 52 of the vessel 54, as shown in FIGS. 10 and 14 and described previously. Or the implant assemblies can be configured so that they are allowed to travel down a vessel and lodge at a furcation as previously described. The arrows 51 shown in FIGS. 10, 11, 14, and 15 indicate the direction of blood flow.

Referring now to FIGS. 35-37, an implant assembly 130 comprises an intracorporal device 131, an elongated "FIG. 8" wire loop 132, and a pair of wing-like wire loops 134. The wing-like wire loops 134 have a longest dimension in a plane orthogonal to the longitudinal axis of the vessel. This longest dimension is, within wide tolerances, on the order of the vessel inner diameter into which the implant assembly 130 is to be introduced, so as to permit the implant assembly to travel down the blood stream until it lodges at a furcation. The "FIG. 8" wire loop 132 has a length which is greater than the diameter of the vessel into which the implant assembly 130 is to be introduced so as to prevent the implant assembly from flipping end-to-end within the vessel. Preferably the length of the "FIG. 8" wire loop 132 is at least twice the diameter of the vessel into which the implant assembly 130 is to be introduced, and in the disclosed embodiment the length of the "FIG. 8" wire loop 132 is approximately five times the diameter of the vessel. This feature is useful to maintain a desired orientation of the implant assembly 130 with respect to the fluid flow within the vessel. In the preferred embodiment, the "FIG. 8" wire loop lies in a plane, and the wing-like wire loops are oriented substantially perpendicular to the plane defined by the wire loops.

Radial Wire Array Structures

Figure 16:
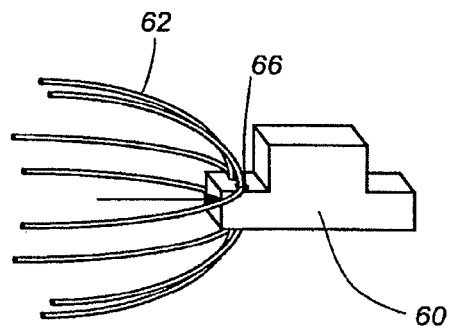
FIG. 16 is an isometric view of a seventh embodiment of an implant assembly of the invention having a radial wire array expansible structure.
Figure 17:
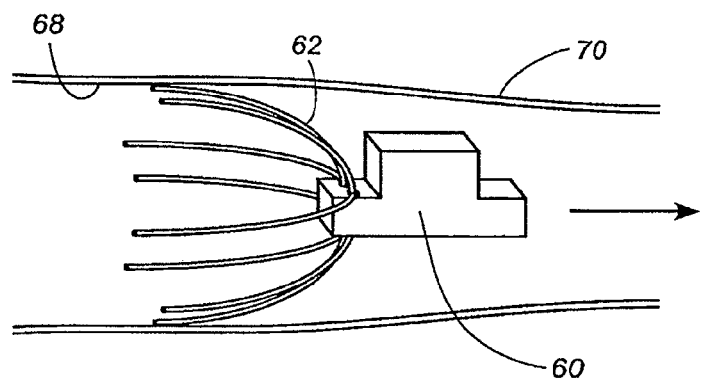
FIG. 17 is a cutaway view of a vessel showing the implant assembly of FIG. 16 fixed therein according to a first embodiment of an implantation method.
Figure 18:
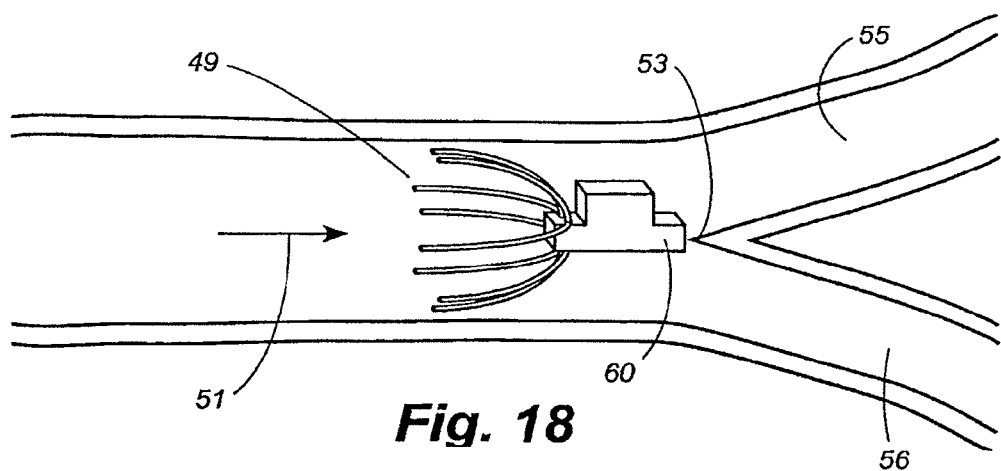
FIG. 18 is a cutaway view of a pulmonary arterial vessel showing the implant assembly of FIG. 16 fixed therein according to an alternate embodiment of an implantation method.
Figure 19:
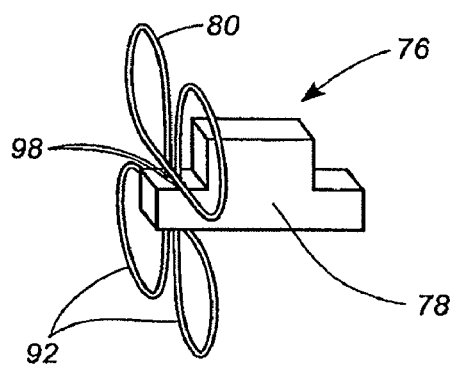
FIG. 19 is an isometric view of an eighth embodiment of an implant assembly of this invention having a daisy petal wire expansible structure.

Another implant assembly—according to this invention includes an intracorporal device and an anchoring structure having a substantially parabolic-shaped profile, as shown in FIGS. 16-18. As illustrated in the Figures, an implant assembly 58 includes an intracorporal device 60 and a radial wire array 62, which includes wire members 64. Members 62 may be attached to the intracorporal device 60 at an anchor point, as described below.

Figure 20:
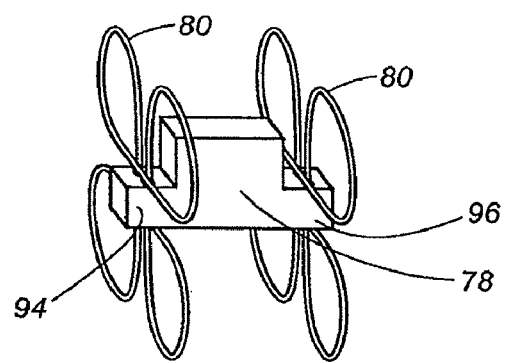
FIG. 20 is an isometric view of a ninth embodiment of an implant assembly of this invention having a daisy petal expansible structure on each end of an intracorporal device.

The radial wire array 62 can be attached to the intracorporal device 60 by threading the wire members 64 through one hole 66 located near the edge of the intracorporal device 60, as shown in FIG. 16. Alternatively, the radial wire array 62 can be attached to the intracorporal device 60 by threading the wire members 64 through two holes 66 located near the edge of the device 60 as shown in FIG. 20. The wire end is press-fit into a coating covering the surface of the device to secure the end. The radial wire array may be formed by crimping a piece of metal at a point substantially midlength of the wire bundle and then threading the wire bundle through a hole near the edge of the intracorporal device, thus lodging the anchor within the silicone material filling the hole. The anchor secures the end of the radial wire between the surface of the device and the coating covering the surface of the device. The crimped metal anchor provides a radiopaque marker for fluoroscopic visualization of the device.

Figure 21:
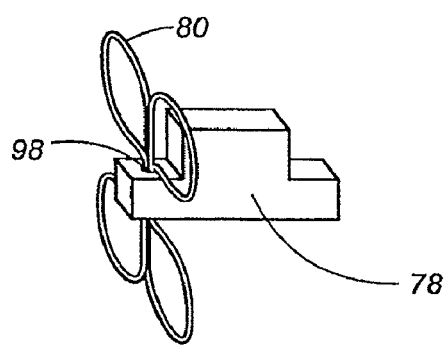
FIG. 21 is an isometric view of a tenth embodiment of an implant assembly of this invention having a daisy petal wire expansible structure.
Figure 22:
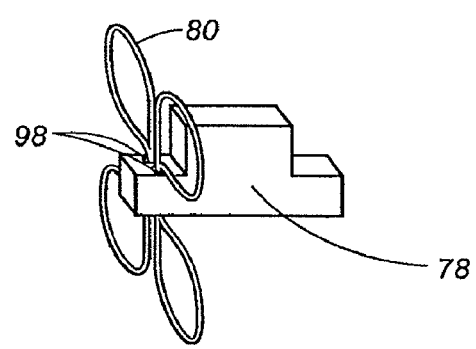
FIG. 22 is an isometric view of an eleventh embodiment of an implant assembly of this invention having a daisy petal wire expansible structure.

Upon deployment of the implant assembly, the implant assembly can be anchored either by an interference fit between the radial wires and the walls of the vessel, as shown in FIG. 21, or by traveling within a vessel until the implant assembly lodges at a furcation, as shown in FIG. 22.

In one embodiment, the radial wire array is self-supporting, as a result of the physical properties of the material. Alternatively, the radial wire array may include a mechanical expansion structure to support the array to expand and contact the vessel wall. For example, a catheter balloon may be inflated to cause a wire structure to attain and maintain an expanded configuration.

The intracorporal device 60 can be positioned outside a radial wire array 62 so that one end 72 of the intracorporal device 60 is fixed to a point at or near the apex of the radial wire array 62, as shown in FIG. 16. The intracorporal device 60 can also be positioned inside the radial wire array so that one end of the device is fixed to a point at or near the apex of the radial wire array, as shown in FIG. 17. In another embodiment, the intracorporal device may have two radial wire arrays 62 attached to the intracorporal device 60 so that one end of the intracorporal device is attached to the apex on the exterior of one of the radial wire arrays and the opposing end of said device is attached to the apex on the interior of the second radial wire array, as shown in FIG. 18.

Daisy Petal Structures

An implant assembly according to another aspect of this invention includes an intracorporal device and an anchoring structure having a daisy petal shape, as shown in FIGS. 23-26. The implant assembly 76 includes an intracorporal device 78 and a daisy petal wire structure 80, which contacts the inner surface 82 of the wall of the vessel 84, as shown in FIG. 27. The implant assembly of this embodiment can be anchored by an interference fit between the implant assembly and the walls of the vessel. In the alternative, the implant assembly can be configured, within wide tolerances, to have a diameter on the order of the vessel inner diameter into which the implant assembly 130 is to be introduced, so as to permit the implant assembly to travel down the blood stream until it lodges at a furcation, as shown in FIG. 28. The arrows 51 shown in FIGS. 27 and 28 indicate the direction of blood flow.

Figure 23:
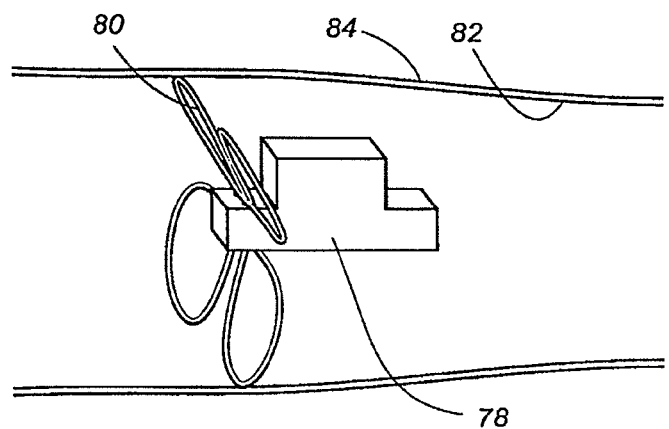
FIG. 23 is a cutaway view of a vessel showing the implant assembly of FIG. 19 fixed therein according to a first embodiment of an implantation method.
Figure 24:
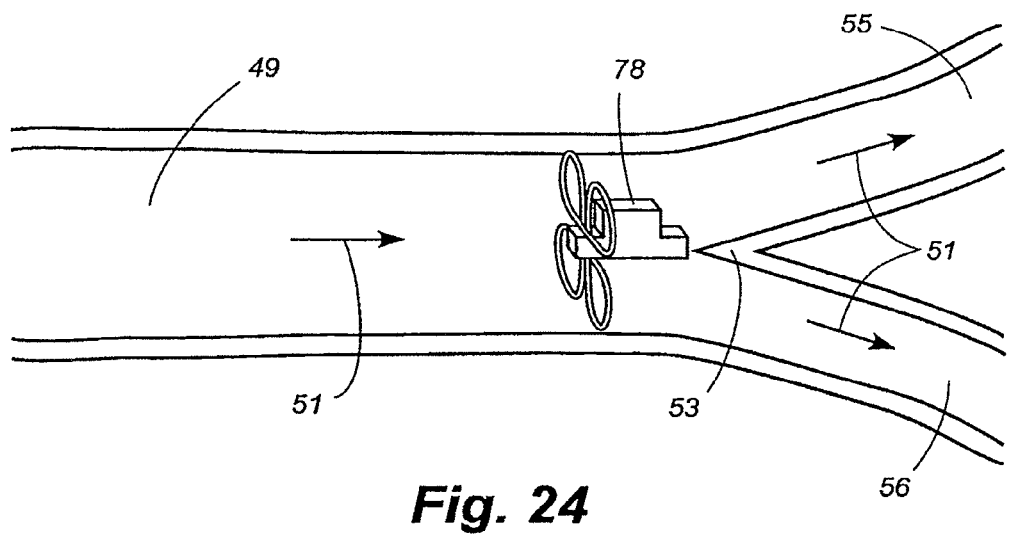
FIG. 24 is a cutaway view of a pulmonary arterial vessel showing the implant assembly of FIG. 19 fixed therein according to an alternate embodiment of an implantation method.

The intracorporal device has a proximal end 86, a distal end 88, and a longitudinal axis 90, as shown in FIG. 23. The daisy petal wire structure 80 is positioned so that the structure lies in a plane normal to the longitudinal axis 90 of the intracorporal device 78. The daisy petal wire structure 80 may be constructed of a single wire or of a plurality of wires. As shown in FIG. 23, the daisy petal wire structure 80 includes a plurality of lobes 92. The structure may have either an even or an odd number of lobes. As shown in FIG. 24, the intracorporal device 78 may have two daisy petal wire structures 80 attached to the device on opposing ends 94, 96 and located along the longitudinal axis 90.

The daisy petal wire structure 80 may be attached to the intracorporal device 78 by threading through a single hole 98 located near the edge of the device 78, as shown in FIG. 25. Alternatively, the daisy petal wire structure 80 may be attached to the intracorporal device 78 by threading through two holes 98 located near the edge of the device 78, as shown in FIG. 23.

In one embodiment, the daisy petal wire structure 80 is attached to the intracorporal device at an anchor point. The anchor is made by crimping a piece of metal to the wire and trimming off the excess wire, so that the crimped-on metal comprises the terminal end of the wire. This metal end also provides a radiopaque marker for fluoroscopic visualization of the device. The wire is threaded through the hole or holes on one end of the intracorporal device and the wire is pulled with sufficient force to bury the anchor fixedly into the coating. The wire is then threaded from top to bottom in a circular fashion, through the hole or holes located on the end of the intracorporal device, to form the daisy petal structure. Upon completion of the daisy petal structure, the free end of the wire is used to create another anchor. The second free end is then pulled back into the coating with sufficient force to bury the second anchor fixedly in the coating. The wire loops are then arranged by mechanical means to create wire members that are substantially evenly distributed radially around the longitudinal axis of the intracorporal device.

Delivery Systems and Methods

Figure 30:
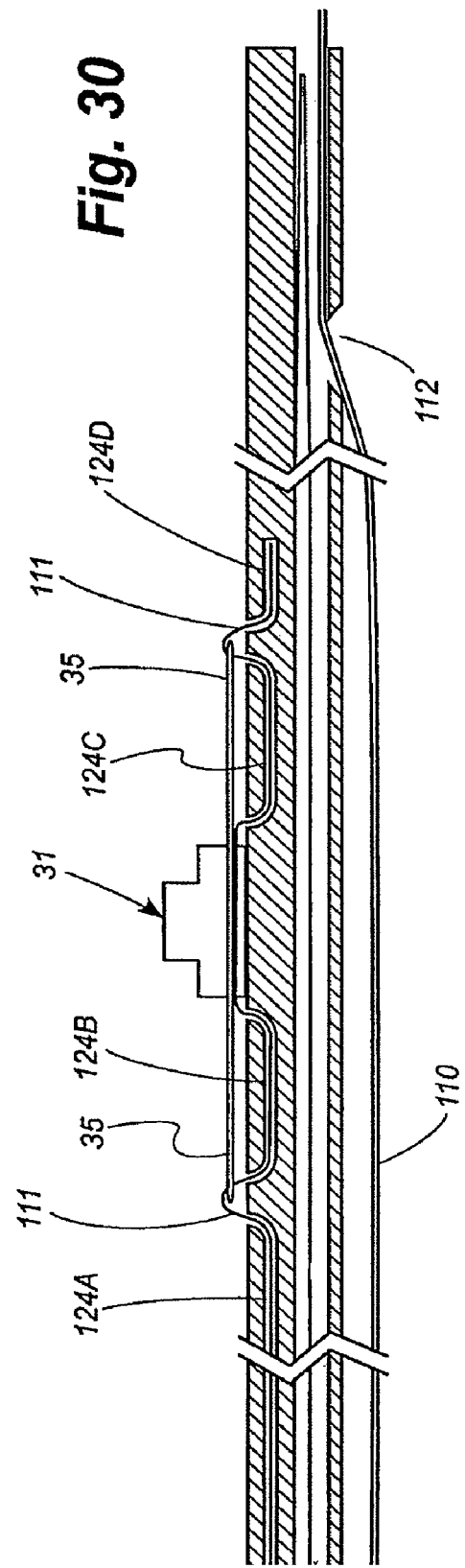
FIG. 30 is a side cross-sectional view of a delivery system for delivering an intracorporal device such as that shown in FIG. 5.
Figure 31:
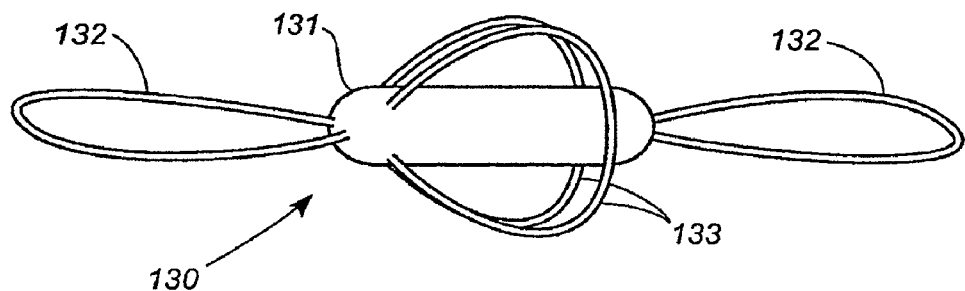
FIG. 31 is a perspective view of an alternate embodiment of an implant assembly according to the present invention.
Figure 32:
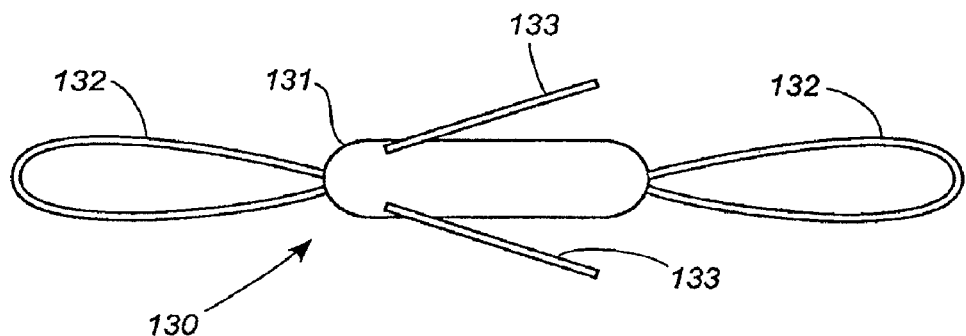
FIG. 32 is a top view of the implant assembly of FIG. 31.
Figure 33:
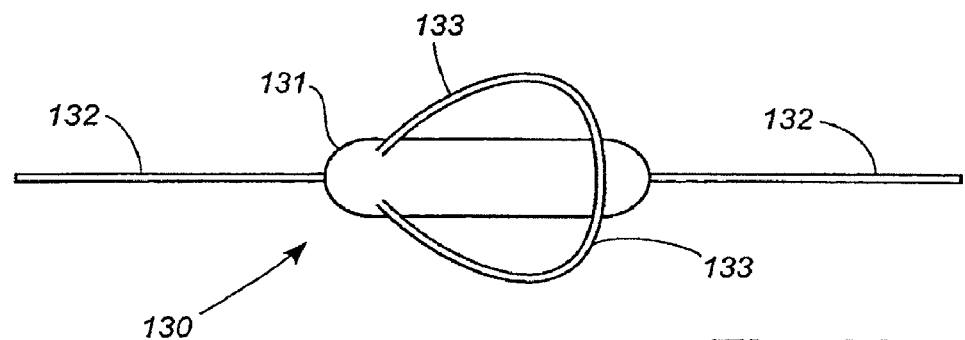
FIG. 33 is a side view of the implant assembly of FIG. 31.

This invention provides a delivery system for securing, delivering and deploying an implant assembly having an anchoring mechanism coupled to an intracorporal device. Referring to FIGS. 29-32, the various components of the delivery system are shown individually. As shown in FIG. 29, the delivery apparatus 100 includes a main lumen 102 adapted to accept a core wire 104 (FIG. 31) and a secondary lumen comprising a first section 106A and a second section 106B and adapted to accept a tether wire 108 (FIG. 30). The core wire 104, shown in FIG. 31, provides columnar stiffness to the delivery assembly 100, thereby facilitating advancement of the delivery assembly through the vasculature. Additionally, the core wire 104 also prevents buckling of the delivery assembly 100 when the tether wire is pulled proximally during the implant assembly deployment. The core wire 104 has a decreasing diameter toward its distal end 105, providing gradual decrease in stiffness from the proximal to the distal end of the delivery assembly 100. The tapered core wire 104 can extend past a guidewire aperture 112 in order to reinforce a potential kink point in the delivery apparatus 100 and to facilitate the advancement of the guidewire into the vasculature. The core wire 104 is fixed in the main lumen 102 using adhesive, thermocompression, or any other suitable fixation mechanism. Fixation of the core wire 104 prevents the core wire from being disturbed by the guidewire 110, shown in FIG. 32, when the guidewire 110 enters the main lumen 102 of the delivery apparatus 100 at the guidewire aperture 112 as shown in FIG. 33.

The tether wire 108, shown in FIG. 30, is slidably positioned within the first secondary lumen portion 106A and exits the first secondary lumen portion at an aperture 114 in the wall of the device. As shown in FIG. 33, the tether wire 108 then passes through the coating of the intracorporal device 30, exiting on the opposite side of the device. The free end 118 of the tether wire 108 enters the second portion 106B of the secondary lumen at the aperture 109.

FIG. 34 shows an alternate embodiment of a delivery apparatus adapted to deploy the intracorporal device 31 of FIGS. 5-7. Because of the length of the wire loops 35 of the intracorporal device 31, the proximal and distal ends of the loops must be secured to the delivery apparatus so that, when the delivery apparatus curves, the loops will follow the curvature of the delivery apparatus. Toward that end, the secondary lumen of the delivery apparatus of FIG. 34 is divided into four sections 124A-D. The tether wire 108 exits the first section 124A of the secondary lumen and passes over and through wire loops 55 to attach the implant assembly 51 to the delivery apparatus 100. The tether wire then enters the second portion 124B of the secondary lumen. The tether wire then exits the second portion 124B of the secondary lumen and passes through the coating of the intracorporal device 31. The tether wire then enters the third portion 124C of the secondary lumen. Next, the tether wire exits the third portion 124C of the secondary lumen, passes over the wire loop 35, and enters the fourth section 124D of the secondary lumen.

In yet another configuration, an outer sleeve may be provided to constrain an expansible structure and is slidably positioned over the double lumen tube.

Deployment and fixation of an implant assembly may be accomplished passively by either an interference fit or lodging at a furcation. In one embodiment, an implant assembly, including an anchoring structure of sufficient size and/or compliance, is delivered into the vessel and allowed to travel in the blood stream until it lodges at a furcation. After lodging in the vessel, blood flow is maintained due to the configuration of the implant assembly. In another embodiment, an implant assembly includes an anchoring structure of sufficient compliance that, upon narrowing of the vessel, produces an interference fit thereby preventing substantially any further progress of the device down the vessel. In a third embodiment, the intracorporal device embolizes without an anchor structure. It could be preferable to eliminate the need for a securing device and to allow the intracorporal device to reside in a vessel that is small enough to prevent further movement of the intracorporal device. As an illustration, it is suspected that the small size of the intracorporal device would have no deleterious effect on lung function due to the redundancy of blood flow in the lungs at the small vessel level.

One method of deploying and fixing an implant assembly according to this invention is described below. Access is gained into the vasculature and a vessel introducer is positioned in the access site. The access site for the vessel introducer may be the right internal jugular vein, the subclavian artery, the right femoral vein, or any other suitable access site. A guidewire is placed in the vasculature and positioned across the desired deployment site with the aid of, e.g., a Swan-Ganz catheter, a diagnostic catheter or any other suitable catheter, such catheter being removed after the guidewire is in position.

The delivery system is loaded into the vessel introducer and navigated to the deployment site. The delivery system length can be increased or decreased according to standard practice depending on the access site chosen. In one embodiment, the deployment site is a vessel, and may be any artery or arteriole in the pulmonary artery vasculature. Optionally, the implant assembly is oriented to a preferred orientation. Then, the implant assembly is deployed by pulling the tether wire proximally to disengage the implant assembly from the delivery apparatus. Upon deployment, the implant assembly is allowed to travel in the vasculature until an interference fit is produced or it lodges at the next furcation in the vasculature, depending on which mode of fixation is intended. The delivery assembly and guidewire are then removed from the body.

In an alternative embodiment of this method, an outer sleeve is provided to constrain an expansible anchor structure so that sliding the outer sleeve proximally allows expansion of the expansible anchor structure. The anchor structure is allowed to expand and the implant assembly travels down the vessel until an interference fit is produced or it lodges at the next furcation in the vasculature, depending on which mode of fixation is intended. The delivery assembly and guidewire are then removed from the body.

The embodiments described above may be employed with a wireless device, as shown in the Figures, or with a wired intracorporal device.

For the purpose of illustration, the pulmonary artery is selected as the deployment site for an intracorporal device. In this example, considerations relevant to the placement of a pressure sensor are disclosed. Other intracorporal devices could be positioned in alternate locations via modifications to the examples disclosed in this document, such locations and methods being obvious to one skilled in the art in light of the disclosure provided herein. To deploy an implant assembly into a pulmonary arterial vessel, the right femoral vein is chosen as the access site. The user gains access to the femoral vein via transcutaneous puncture or cut-down. A vessel introducer is placed in the site. A Swan-Ganz or guiding catheter is maneuvered into the pulmonary artery. The path to the pulmonary artery is as follows: the femoral vein leads to the inferior vena cava. From the inferior vena cava, the catheter travels through the right atrium to the right ventricle and, finally, to the pulmonary artery. At this point, the right or left branch of the pulmonary artery is selected, and the Swan-Ganz or guiding catheter is positioned in the descending branch of either the right or left pulmonary artery. A guidewire is placed at the deployment site, and the Swan-Ganz or guiding catheter is removed. At this point, the delivery catheter is loaded over the proximal end of the guidewire. Optionally, a guiding catheter can be loaded over the proximal ends of the guidewire and delivery catheter to a point where the distal end of this guiding catheter is located immediately proximal to the implant assembly on the delivery catheter. The delivery catheter (and, optionally, guiding catheter) is tracked over the guidewire to the deployment site. The tether is pulled proximally to disengage the implant assembly from the delivery apparatus.

The lung can be divided into three zones depending on the relationship between the pulmonary artery pressure, alveolar pressure, and pulmonary venous pressure. In Zone 1, the uppermost portion of the lung, the alveolar pressure is greater than that of either the pulmonary artery or the pulmonary vein, causing collapse of the vessel during each respiratory cycle. (Zone 1 conditions do not normally occur in humans.) In Zone 2, the alveolar pressure is less than the pulmonary artery pressure and greater than the pulmonary venous pressure leading to a state of partial vessel collapse. However, in Zone 3, at the bottom of the lungs, all blood vessels remain fully open during the entire respiratory cycle because of the fact that both the pulmonary artery and venous pressures are greater than the alveolar pressure. The implant assembly is released into the descending branch of either the right or left pulmonary artery because this will cause the intracorporal device to lodge in Zone 3 of the lungs. It is not known whether vessel collapse would cause any deleterious effect on the pressure measured by the sensor, but the present invention eliminates this unknown by positioning the sensor in a location where the possibility of this phenomenon is minimized.

Unless otherwise stated, terms used herein such as "top," "bottom," "upper," "lower," "left," "right," "front," "back," "proximal," "distal," and the like are used only for convenience of description and are not intended to limit the invention to any particular orientation.

Finally, it will be understood that the preferred embodiment has been disclosed by way of example, and that other modifications may occur to those skilled in the art without departing from the scope and spirit of the appended claims.

What is claimed is:

1. An in vivo implant assembly for deployment within a vessel, the vessel having an inner diameter, comprising:
   an intracorporal device body having a first end and a second opposing end, the intracorporal device body further having a longitudinal axis and a diameter smaller than the inner diameter of the vessel into which the implant assembly is intended to be positioned; and
   a means for passively creating an interference fit between the in vivo implant assembly and the inner diameter of the vessel, comprising: a longitudinal anchor structure, wherein a proximate end portion of the longitudinal anchor structure is positionally fixed relative to a top surface of the intracorporal device, wherein a distal end portion of the longitudinal anchor structure extends distally outwardly from the proximate end portion of the longitudinal anchor structure and a respective end of the intracoporeal device body to form a loop that is positioned in an operative plane that is parallel to the longitudinal axis of the intracorporal device body, wherein the distal-most end of the distal end portion forms a continuously curved tip, wherein at least a portion of the longitudinal anchor structure has a diameter that is at least as large as the inner diameter of the vessel into which the implant assembly is intended to be operatively located, and wherein the intracorporal device is adapted to be permanently fixed relative to the position of the created interference fit within the vessel.

2. The implant assembly of claim 1, wherein the overall longitudinal length of the intracorporal device body and the longitudinal anchor structure is greater than the inner diameter of the vessel.

3. The implant assembly of claim 2, wherein the overall longitudinal length of the intracorporal device body and the longitudinal anchor structure is at least two times the inner diameter of the a vessel into which the implant assembly is intended to be operatively located.

4. The implant assembly of claim 3, wherein the overall longitudinal length of the intracorporal device body and the longitudinal anchor structure is less than about approximately five times the inner diameter of the a vessel into which the implant assembly is intended to be operatively located.

5. The implant assembly of claim 1, wherein the longitudinal anchor structure comprises a first wire loop extending longitudinally from the first end of the intracorporal device body.

6. The implant assembly of claim 5, wherein the longitudinal anchor structure further comprises a second wire loop extending longitudinally from the second end of the intracorporal device body.

7. The implant assembly of claim 1, wherein the longitudinal anchor structure is sufficiently stiff to prevent downstream movement of the in vivo implant assembly after the interference fit is created.

8. The implant assembly of claim 7, wherein the in vivo implant assembly obstructs less that 50% of the cross-sectional area of the inner diameter of the vessel into which the implant assembly is positioned after the interference fit is created.

9. The implant assembly of claim 8, wherein the vessel is a human pulmonary arterial vessel.

10. The implant assembly of claim 1, further comprising means for preventing substantial rotation of the implant assembly about an axis of rotation perpendicular to a longitudinal axis of the vessel.

11. An in vivo implant assembly for deployment within a vessel, the vessel having an inner diameter, comprising:
an intracorporal device body having a first end and a second opposing end, the intracorporal device body further having a longitudinal axis and a body diameter smaller than the inner diameter of the vessel into which the implant assembly is intended to be deployed; and
a means for passively creating an interference fit between the in vivo implant assembly and the inner diameter of the vessel, comprising: a longitudinal anchor structure that extends distally outwardly longitudinally from a proximate end portion of the longitudinal anchor to form a loop that forms a continuously curved tip at the distal-most end of the longitudinal anchor structure, wherein the longitudinal length of the longitudinal anchor structure is greater than the body diameter, wherein at least a portion of the longitudinal anchor structure has a diameter that is at least as large as the inner diameter of the vessel into which the implant assembly is intended to be deployed, and wherein the intracorporal device is adapted to be permanently fixed relative to the position of the created interference fit within the vessel.

12. The implant assembly of claim 11, wherein the loop of the longitudinal anchor structure is positioned substantially parallel to the longitudinal axis of the intracorporal device body.

13. The implant assembly of claim 12, wherein the longitudinal anchor structure comprises a first wire loop extending longitudinally from the first end of the intracorporal device body.

14. The implant assembly of claim 13, wherein the longitudinal anchor structure further comprises a second wire loop extending longitudinally from the second end of the intracorporal device body.

15. The implant assembly of claim 11, wherein the overall longitudinal length of the intracorporal device body and the longitudinal anchor structure is at least two times the inner diameter of the a vessel into which the implant assembly is intended to be operatively located.

16. The implant assembly of claim 11, wherein a proximate end portion of the longitudinal anchor structure is positionally fixed relative to a top surface of the intracorporal device.

17. An in vivo implant assembly for deployment within a vessel, the vessel having an inner diameter, comprising:
an intracorporal device body having a first end and a second opposing end, a longitudinal axis and a diameter smaller than the inner diameter of the vessel; and
a longitudinal anchor structure extending distally outwardly longitudinally from the proximate end portion of the longitudinal anchor structure to form a loop that has a continuously curved tip at the distal-most end of the longitudinal anchor structure, wherein the loop is configured to resiliently contact and form an interference fit with a portion of the operative vessel, wherein the overall longitudinal length of the intracorporal device body and the longitudinal anchor structure is greater than the inner diameter of the vessel, wherein at least a portion of the longitudinal anchor structure has a diameter that is at least as large as the inner diameter of the vessel into which the implant assembly is intended to be deployed, and wherein the intracorporal device is adapted to be permanently fixed relative to the position of the created interference fit within the vessel.

18. The implant assembly of claim 17, wherein the loop extends longitudinally from the first end of the intracorporal device body.

19. The implant assembly of claim 18, wherein the loop extends longitudinally from the second end of the intracorporal device body.

20. The implant assembly of claim 17, wherein the loop extends longitudinally from the first or second end of the intracorporal device body.

21. The implant assembly of claim 17, wherein the proximate end portion of the longitudinal anchor structure is anchored to at least one end of the intracorporal device body.

22. The implant assembly of claim 17, wherein the operative inner diameter is less than the deployment inner diameter.

23. A method of implanting an in vivo implant assembly within a vessel having an inner diameter, comprising:
providing an in vivo implant assembly comprising:
an intracorporal device body having a first end and a second opposing end, a longitudinal axis and a body diameter smaller than the inner diameter of the vessel into which the implant assembly is intended to be deployed; and
a means for passively creating an interference fit between the in vivo implant assembly and the inner diameter of the vessel, comprising: a longitudinal anchor structure configured to extend distally outwardly longitudinally from the first or second end of the intracorporal device body and having a continuously curved tip at the distal-most end of the longitudinal anchor structure, wherein the overall longitudinal length of the intracorporal device body and the longitudinal anchor structure is greater than the inner diameter of the vessel, wherein at least a portion of the longitudinal anchor structure has a diameter that is at least as large as the inner diameter of the vessel into which the implant assembly is intended to be deployed, and wherein the intracorporal device is permanently fixed relative to the fixation position of the created interference fit within the vessel;
releasing the implant assembly into the vessel at a release position; and permitting the implant assembly to form the interference fit with the inner diameter of the vessel at the fixation position.

24. The method of claim 23, wherein the release position is upstream of the fixation position, further comprising permitting the implant assembly to move downstream within the vessel along with the flow of blood in the vessel.

25. The method of claim 24, further comprising permitting the implant assembly to form the fixation position at a downstream furcation in which the vessel divides into sub-vessels.

26. The method of claim 23, wherein the release position is proximate the fixation position.

27. The method of claim 23, comprising the further step of preventing the implant assembly from substantial rotation about an axis of rotation perpendicular to a longitudinal axis of the vessel.

* * * * *